US012629075B2

(12) United States Patent
Jeong et al.

(10) Patent No.: US 12,629,075 B2
(45) Date of Patent: May 19, 2026

(54) SENSOR FOR SIMULTANEOUSLY MEASURING ELECTROCARDIOGRAM AND MECHANOCARDIOGRAM AND METHOD OF MANUFACTURING SAME

(71) Applicant: POSTECH Research and Business Development Foundation, Pohang-si (KR)

(72) Inventors: Unyong Jeong, Pohang-si (KR); Sung-Min Park, Pohang-si (KR); Joosung Oh, Pohang-si (KR); Junho Kim, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 268 days.

(21) Appl. No.: 18/380,768

(22) Filed: Oct. 17, 2023

(65) Prior Publication Data

US 2024/0164681 A1     May 23, 2024

(30) Foreign Application Priority Data

Nov. 17, 2022   (KR) ........................ 10-2022-0154627
Feb. 20, 2023   (KR) ........................ 10-2023-0022067
Sep. 6, 2023    (KR) ........................ 10-2023-0118435

(51) Int. Cl.
  *B82Y 30/00*        (2011.01)
  *A61B 5/00*         (2006.01)
      (Continued)
(52) U.S. Cl.
  CPC ........... *A61B 5/268* (2021.01); *A61B 5/0205* (2013.01); *A61B 5/1102* (2013.01); *A61B 5/27* (2021.01);
      (Continued)

(58) Field of Classification Search
  CPC ........... A61B 5/25; A61B 5/263; A61B 5/268; A61B 5/27; A61B 5/28; A61B 5/6833;
      (Continued)

(56) References Cited

U.S. PATENT DOCUMENTS

2008/0187996 A1*  8/2008  Baca .................... C12N 5/0075
                                                              435/396
2023/0043933 A1*  2/2023  Jeong ................... D06M 15/61
2024/0285180 A1*  8/2024  Closson ................ A61B 5/024

FOREIGN PATENT DOCUMENTS

WO        2018/193271       10/2018
WO    WO 2021/085877     *  6/2021

OTHER PUBLICATIONS

KIPO, Office Action of KR 10-2023-0118435 dated Apr. 17, 2025, total 5 pages.

(Continued)

*Primary Examiner* — Allen Porter
(74) *Attorney, Agent, or Firm* — LEX IP MEISTER, PLLC

(57) ABSTRACT

Proposed are a sensor for simultaneously measuring electrocardiogram and mechanocardiogram and a method of manufacturing the same. The sensor for simultaneously measuring electrocardiogram and mechanocardiogram includes a base mat including nanofibers including a polymer, and having a porous structure, and a conductive pattern portion impregnated into the base mat to a predetermined depth and including a first pattern for measuring the electrocardiogram and a second pattern for measuring the mechanocardiogram. Each of the first pattern and the second pattern includes nanofibers including the polymer, and a conductor located between the nanofibers. The sensor for simultaneously measuring electrocardiogram and mechanocardiogram has excellent mechanical and electrical stability against stretching. Thus, the long-term use of the sensor as (Continued)

an implantable electrode enables stable simultaneous measurement of electrocardiogram and mechanocardiogram.

12 Claims, 16 Drawing Sheets

(51) Int. Cl.
  *A61B 5/0205* (2006.01)
  *A61B 5/11* (2006.01)
  *A61B 5/268* (2021.01)
  *A61B 5/27* (2021.01)
  *A61B 5/287* (2021.01)

(52) U.S. Cl.
  CPC .............. *A61B 5/287* (2021.01); *A61B 5/688* (2013.01); *A61B 2562/0285* (2013.01); *A61B 2562/125* (2013.01)

(58) Field of Classification Search
  CPC ...... A61B 2562/0209; A61B 2562/125; A61B 2562/164; B82Y 30/00
  See application file for complete search history.

(56) References Cited

OTHER PUBLICATIONS

Joosung Oh et al., "Subcutaneous mechano-electrocardiogram (MECG) sensor for complementary cardiac diagnosis", Biosensors and Bioelectronics, vol. 236, pp. 115443, Sep. 2023, doi: https://doi.org/10.1016/j.bios.2023.115443.

* cited by examiner

SENSOR FOR SIMULTANEOUSLY MEASURING ELECTROCARDIOGRAM AND MECHANOCARDIOGRAM AND METHOD OF MANUFACTURING SAME

CROSS REFERENCE TO RELATED APPLICATION

The present application claims priority to Korean Patent Applications No. 10-2022-0154627, filed Nov. 17, 2022, No. 10-2023-0022067, filed Feb. 20, 2023, and No. 10-2023-0118435, filed Sep. 6, 2023, the entire contents of which is incorporated herein for all purposes by this reference.

BACKGROUND OF THE INVENTION

Field of the Invention

The present disclosure relates to a sensor for simultaneously measuring electrocardiogram and mechanocardiogram and a method of manufacturing the same.

Description of the Related Art

Electrocardiogram (ECG) is widely used to measure signs of heart disease. The ECG is a technology that measures electrical signals generated from the heart. In order to measure ECG abnormalities that appear intermittently in diagnosing arrhythmia, a technology that continuously measures ECG is required.

Conventional electrodes used in ECG are divided into two types: a wearable electrode and an implantable electrode. The wearable electrode often cannot be used when exposed to water or during intense exercise, so the implantable electrode is widely used for continuous and stable measurement. As the implantable electrode, a metal structure such as stainless steel is widely used. Despite its high electrical stability, it easily causes inflammatory reactions due to differences in mechanical properties from body tissues, necessitating the use of antibiotics. Therefore, a new type of implantable electrode is needed for continuous ECG measurement.

Meanwhile, ECG cannot measure mechanical problems in the heart. A typical example of a mechanical problem in the heart is a cardiovascular problem that occurs as a side effect of anticancer treatment. The cardiovascular problem cannot be measured with ECG, and mechanical abnormalities have to be measured separately. A technology to measure such mechanical abnormalities includes echocardiography using an ultrasonic device. However, mobile echocardiography devices do not yet exist due to issues with the size of equipment and the expertise of equipment users in operating the devices.

Accordingly, there is a need for an implantable sensor that has electrical and mechanical stability and can simultaneously measure electrocardiogram (ECG) and mechanocardiogram (MCG).

The foregoing is intended merely to aid in the understanding of the background of the present disclosure, and is not intended to mean that the present disclosure falls within the purview of the related art that is already known to those skilled in the art.

SUMMARY OF THE INVENTION

Accordingly, the present disclosure has been made keeping in mind the above problems occurring in the related art, and the present disclosure provides an implantable sensor that has electrical and mechanical stability and can simultaneously measure electrocardiogram and mechanocardiogram.

Another objective of the present disclosure is to provide a method of manufacturing an implantable sensor that can simultaneously measure electrocardiogram and mechanocardiogram.

In order to achieve the above objectives, according to one aspect of the present disclosure, there is provided a sensor for simultaneously measuring electrocardiogram and mechanocardiogram, the sensor including: a base mat including nanofibers including a polymer, and having a porous structure; and a conductive pattern portion impregnated into the base mat to a predetermined depth and including a first pattern for measuring the electrocardiogram and a second pattern for measuring the mechanocardiogram. Here, each of the first pattern and the second pattern may include: nanofibers including the polymer; and a conductor located between the nanofibers.

In addition, the polymer of the base mat may be bound to the polymer of the conductive pattern portion by chain entanglement or covalent bonding.

In addition, the first pattern may have a thickness larger than that of the second pattern.

In addition, the first pattern may have a width larger than that of the second pattern.

In addition, the first pattern may have a thickness in a range of 10 to 20 μm, and the second pattern may have a thickness in a range of 1 to 8 μm.

In addition, the first pattern may have a width in a range of 500 μm to 5 mm, and the second pattern may have a width in a range of 500 μm to 5 mm.

In addition, the first pattern may include a "□" shape, and the second pattern may include a square shape.

In addition, the nanofibers of the base mat, the nanofibers of the first pattern, and the nanofibers of the second pattern may be the same.

In addition, the nanofibers of the base mat, the nanofibers of the first pattern, and the nanofibers of the second pattern may each independently further include a polyalkyleneamine obtained by crosslinking the polymer.

In addition, the crosslinking may each independently include at least one selected from the group consisting of inter-crosslinking which crosslinks surfaces of the nanofibers with each other and intra-crosslinking which crosslinks the polymer within a single nanofiber.

In addition, the polyalkyleneimines may be the same or different from each other, and may each independently include at least one selected from the group consisting of linear polyalkyleneamine, comb polyalkyleneamine, branched polyalkyleneamine, and dendrimer polyalkyleneamine, preferably branched polyalkyleneamine.

In addition, the polyalkyleneimines may be the same or different from each other, and may each independently include at least one selected from the group consisting of polyethyleneimine and polypropyleneimine.

In addition, surfaces of the nanofibers may be treated with a silane compound including an amine group.

In addition, the silane compound including the amine group may include at least one selected from the group consisting of (3-aminopropyl)triethoxysilane (APTES), (3aminopropyl)trimethoxysilane (APTMS), N-(2-amino-ethyl) 3aminopropyltrimethoxysilane (AEAPTMS), and N-(2-aminoethyl)-11aminoundecyltrimethoxysilane.

In addition, the polymer may be an elastic body.

In addition, the polymer may include at least one selected from the group consisting of polystyrene-block-polybutadiene-block-polystyrene (SBS), polystyrene-block-polyisoprene-block-polystyrene (SIS), polystyrene-block-poly(ethylene butylene)-block-polystyrene (SEBS), polystyrene-block-polybutadiene (SBR), polystyrene-block-poly(ethylene propylene)-block-polystyrene (SEPS), poly(styrene methyl methacrylate) (PSMMA), poly(styrene acrylonitrile) (PSAN), polyurethane, silicone rubber, and butadiene rubber.

In addition, the polymer may further include an organic acid anhydride grafted to a main chain.

In addition, the organic acid anhydride may include at least one selected from the group consisting of maleic anhydride, succinic anhydride, acetic anhydride, naphthalenetetracarboxylic dianhydride, and ethanoic anhydride.

In addition, the conductor may include at least one selected from the group consisting of gold (Au), silver (Ag), copper (Cu), platinum (Pt), palladium (Pd), nickel (Ni), indium (In), aluminum (Al), iron (Fe), rhodium (Rh), ruthenium (Ru), osmium (Os), cobalt (Co), molybdenum (Mo), zinc (Zn), vanadium (V), tungsten (W), titanium (Ti), manganese (Mn), chromium (Cr), graphene, and carbon nanotubes (CNT).

In addition, the sensor may further include an adhesive portion located on a surface of the sensor.

In addition, the sensor may be a subcutaneously implantable sensor.

According to another aspect of the present disclosure, there is provided a method of manufacturing a sensor for simultaneously measuring electrocardiogram and mechanocardiogram, the method including: (a) preparing a base mat including nanofibers by electrospinning a polymer solution including a polymer; and (b) depositing a conductor on the base mat to form a conductive pattern portion impregnated into the base mat to a predetermined depth and including a first pattern for measuring the electrocardiogram and a second pattern for measuring the mechanocardiogram. Here, each of the first pattern and the second pattern may include: nanofibers including the polymer; and a conductor located between the nanofibers.

In addition, the first pattern may be formed by performing the deposition for 250 to 750 seconds, and the second pattern may be formed by performing the deposition for 10 to 200 seconds.

In addition, the method may further include: after step (a), (a') preparing a porous mat including a polymer crosslinked with a polyalkyleneamine by immersing, swelling, and crosslinking the base mat in a polyalkyleneamine solution.

In addition, the method may further include: after step (a), (a") treating the base mat with a silane compound including an amine group.

In addition, the method may further include: after step (b), (b') forming an adhesive portion on a surface of the sensor.

According to the sensor for simultaneously measuring electrocardiogram and mechanocardiogram according to the present disclosure, a nanofiber mat produced by electrospinning is chemically treated to provide excellent mechanical and electrical stability against stretching. The long-term use of the sensor as an implantable electrode enables stable simultaneous measurement of electrocardiogram and mechanocardiogram.

In detail, a polymer including an organic acid anhydride grafted to a main chain is electrospun to form a permeable structure with a low Young's modulus. By reacting this structure with polyalkyleneamine, a bond between the organic acid anhydride and the amine is induced, and individual nanofibers are crosslinked with each other to provide mechanical stability.

In addition, the nanofiber mat is additionally treated with a silane compound including an amine group to provide additional amine groups on surfaces thereof. The surface treatment can improve electrical stability by inducing electrostatic attraction with a conductor (gold).

In addition, according to the method of manufacturing the sensor for simultaneously measuring electrocardiogram and mechanocardiogram according to the present disclosure, it is possible to manufacture a sensor that can simultaneously measure strain and action potential on one substrate by producing different conductive patterns by adjusting the deposition time of the conductor.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Hereinafter, exemplary embodiments of the present disclosure will be described in detail with reference to the accompanying drawings such that the present disclosure can be easily embodied by one of ordinary skill in the art to which the present disclosure belongs.

However, the following description is not intended to limit the embodiments to one preferred embodiment. In the following description, detailed descriptions of known functions and components incorporated herein will be omitted when it may make the subject matter of the present disclosure unclear.

The terminology used herein is for the purpose of describing particular embodiments only and is not intended to be limiting. As used herein, the singular forms are intended to include the plural forms as well, unless the context clearly indicates otherwise. It will be understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Further, although the terms first, second, etc. may be used herein to describe various elements, these elements should not be limited by these terms. These terms are only used to distinguish one element from another element. For instance, a first element discussed below could be termed a second element without departing from the teachings of the present disclosure. Similarly, the second element could also be termed the first element.

Further, it will be understood that when one element is referred to as being "formed" or "layered" on another element, it may be formed or layered so as to be directly attached to the entire surface or one surface of the other element, or intervening elements may be present therebetween.

Hereinafter, a sensor for simultaneously measuring electrocardiogram and mechanocardiogram and a method of manufacturing the same will be described in detail. The following embodiments are merely exemplary embodiments of the present disclosure. Therefore, the present disclosure is not limited to the following embodiments, and the present disclosure is defined only by the scope of the appended claims.

Figure 1:
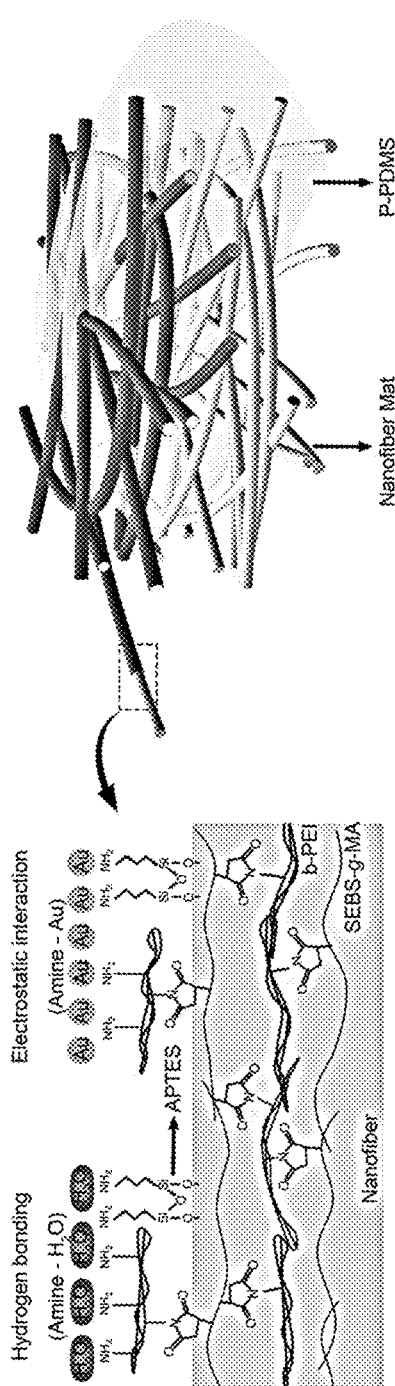
FIG. 1 is a schematic view illustrating a sensor for simultaneously measuring electrocardiogram and mechanocardiogram according to an embodiment of the present disclosure.
Figure 3:
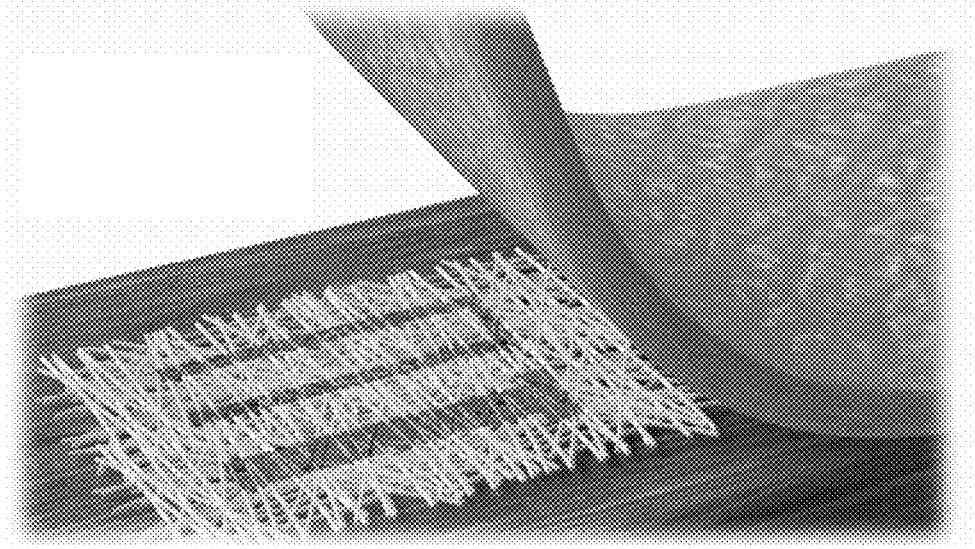
FIG. 3 is a schematic view illustrating subcutaneous implantation of the sensor for simultaneously measuring electrocardiogram and mechanocardiogram according to the embodiment of the present disclosure.

FIG. 1 is a schematic view illustrating a sensor for simultaneously measuring electrocardiogram and mechanocardiogram according to an embodiment of the present disclosure. FIG. 3 is a schematic view illustrating subcutaneous implantation of the sensor for simultaneously measuring electrocardiogram and mechanocardiogram according to the embodiment of the present disclosure.

Referring to FIGS. 1 and 3, the present disclosure provides a sensor for simultaneously measuring electrocardiogram and mechanocardiogram, the sensor including: a base mat including nanofibers including a polymer, and having a porous structure; and a conductive pattern portion impregnated into the base mat to a predetermined depth and including a first pattern for measuring the electrocardiogram and a second pattern for measuring the mechanocardiogram. Each of the first pattern and the second pattern includes: nanofibers including the polymer; and a conductor located between the nanofibers.

In addition, the polymer of the base mat may be bound to the polymer of the conductive pattern portion by chain entanglement or covalent bonding.

In addition, the first pattern may have a thickness larger than that of the second pattern.

In addition, the first pattern may have a width larger than that of the second pattern.

In addition, the first pattern may have a thickness in the range of 10 to 20 μm. When the thickness of the first pattern is less than 10 μm, it is not preferable because the conduction value may change due to the strain, making it difficult to measure the electrocardiogram. Meanwhile, the conductive pattern portion is formed by depositing a conductor (gold). Even when the deposition is carried out for a long period of time, a thickness equal to or larger than a certain level (20 μm) cannot be obtained. Therefore, it is not preferable that the thickness of the first pattern exceeds 20 μm.

In addition, the second pattern may have a thickness in the range of 1 to 8 μm. When the thickness of the second pattern is less than 1 μm, it is not preferable because it is difficult to secure conductivity due to the thin thickness. When it exceeds 8 μm, it is not preferable because sensitivity to the strain decreases.

In addition, the first pattern may have a width in the range of 500 μm to 5 mm. When the width of the first pattern is less than 500 μm, it is not preferable because the conduction value changes due to the strain, making it difficult to measure the electrocardiogram. When it exceeds 5 mm, it is not preferable because an increase in electrocardiogram sensitivity is insignificant compared to the amount of conductor used to form the pattern, making it economically inefficient.

In addition, the second pattern may have a width in the range of 500 μm to 5 mm. When the width of the second pattern is less than 500 μm, it is not preferable because it is difficult to secure conductivity due to the narrow width. When it exceeds 5 mm, it is not preferable because sensitivity to the strain decreases.

In addition, the first pattern may include a "□" shape, and the second pattern may include a square shape.

In addition, the nanofibers of the base mat, the nanofibers of the first pattern, and the nanofibers of the second pattern may be the same.

In addition, the nanofibers of the base mat, the nanofibers of the first pattern, and the nanofibers of the second pattern may each independently further include a polyalkyleneamine obtained by crosslinking the polymer.

In addition, the crosslinking may each independently include at least one selected from the group consisting of inter-crosslinking which crosslinks surfaces of the nanofibers with each other and intra-crosslinking which crosslinks the polymer within a single nanofiber.

In addition, the polyalkyleneimines may be the same or different from each other, and may each independently include at least one selected from the group consisting of linear polyalkyleneamine, comb polyalkyleneamine, branched polyalkyleneamine, and dendrimer polyalkyleneamine, preferably branched polyalkyleneamine.

In addition, the polyalkyleneimines may be the same or different from each other, and may each independently include at least one selected from the group consisting of polyethyleneimine and polypropyleneimine, preferably polyethyleneimine.

In addition, surfaces of the nanofibers may be treated with a silane compound including an amine group. When the surfaces of the nanofibers are treated with the silane compound including the amine group, electrical stability can be improved by inducing electrostatic attraction with the conductor (gold).

In addition, the silane compound including the amine group may include at least one selected from the group consisting of (3-aminopropyl)triethoxysilane (APTES), (3aminopropyl)trimethoxysilane (APTMS), N-(2-aminoethyl) 3aminopropyltrimethoxysilane (AEAPTMS), and N-(2-aminoethyl)-11aminoundecyltrimethoxysilane, preferably (3-aminopropyl)triethoxysilane (APTES).

In addition, the polymer may be an elastic body.

In addition, the polymer may include at least one selected from the group consisting of polystyrene-block-polybutadiene-block-polystyrene (SBS), polystyrene-block-polyisoprene-block-polystyrene (SIS), polystyrene-block-poly(ethylene butylene)-block-polystyrene (SEBS), polystyrene-block-polybutadiene (SBR), polystyrene-block-poly (ethylene propylene)-block-polystyrene (SEPS), poly (styrene methyl methacrylate) (PSMMA), poly(styrene acrylonitrile) (PSAN), polyurethane, silicone rubber, and butadiene rubber, preferably polystyrene-block-poly(ethylene butylene)-block-polystyrene (SEBS).

In addition, the polymer may further include an organic acid anhydride grafted to a main chain.

In addition, the organic acid anhydride may include at least one selected from the group consisting of maleic anhydride, succinic anhydride, acetic anhydride, naphthalenetetracarboxylic dianhydride, and ethanoic anhydride, preferably maleic anhydride.

In addition, the conductor may include at least one selected from the group consisting of gold (Au), silver (Ag), copper (Cu), platinum (Pt), palladium (Pd), nickel (Ni), indium (In), aluminum (Al), iron (Fe), rhodium (Rh), ruthenium (Ru), osmium (Os), cobalt (Co), molybdenum (Mo), zinc (Zn), vanadium (V), tungsten (W), titanium (Ti), manganese (Mn), chromium (Cr), graphene, and carbon nanotubes (CNT), preferably gold (Au).

In addition, the sensor may further include an adhesive portion located on a surface of the sensor.

In addition, the sensor may be a subcutaneously implantable sensor.

Figure 2:
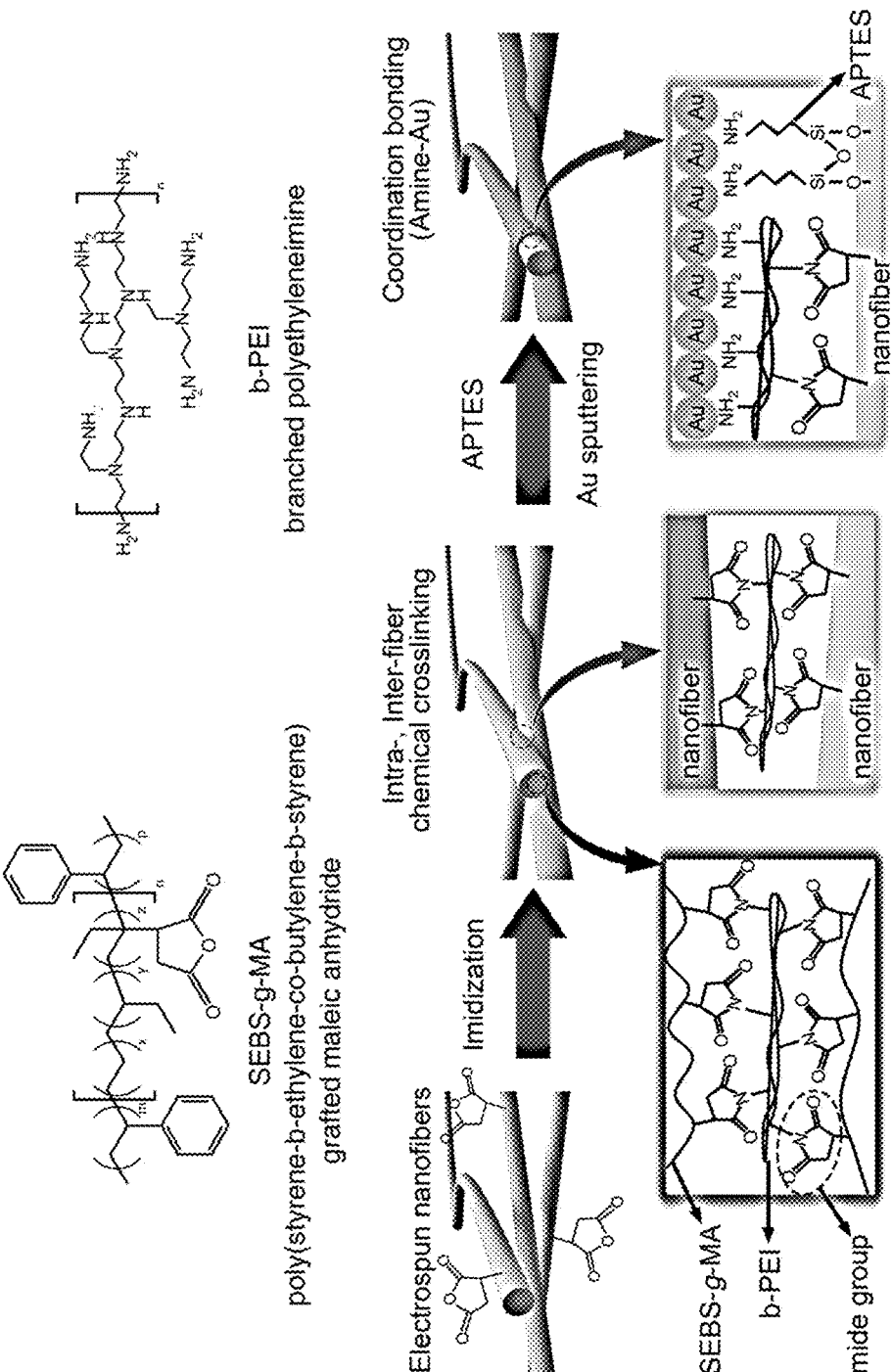
FIG. 2 is a schematic view illustrating a method of manufacturing a sensor for simultaneously measuring electrocardiogram and mechanocardiogram according to an embodiment of the present disclosure.

FIG. 2 is a schematic view illustrating a method of manufacturing a sensor for simultaneously measuring electrocardiogram and mechanocardiogram according to an embodiment of the present disclosure.

Referring to FIG. 2, the present disclosure provides a method of manufacturing a sensor for simultaneously measuring electrocardiogram and mechanocardiogram, the method including: (a) preparing a base mat including nanofibers by electrospinning a polymer solution including a polymer; and (b) depositing a conductor on the base mat to form a conductive pattern portion impregnated into the base mat to a predetermined depth and including a first pattern for measuring the electrocardiogram and a second pattern for measuring the mechanocardiogram. Each of the first pattern and the second pattern includes nanofibers including the polymer; and a conductor located between the nanofibers.

In addition, the first pattern may be formed by performing the deposition for 250 to 750 seconds, preferably 450 to 600 seconds. When the duration time of the deposition is less than 250 seconds, it is not preferable because a thin pattern is formed and the conduction value changes due to the strain, making it difficult to measure the electrocardiogram. When it exceeds 600 seconds, the conductor is not deposited deeper than a certain thickness (20 μm), so the maximum thickness of the formed pattern is the same. That is, it is not preferable because an increase in the thickness of the formed pattern is insignificant compared to the duration time, making it economically inefficient.

In addition, the second pattern may be formed by performing the deposition for 10 to 200 seconds, preferably 50 to 150 seconds. When the duration time of the deposition is less than 10 seconds, it is not preferable because a thin pattern is formed, making it difficult to secure conductivity. When it exceeds 200 seconds, it is not preferable because sensitivity to deformation decreases.

In addition, the method may further include, after step (a), (a') preparing a porous mat including a polymer crosslinked with a polyalkyleneamine by immersing, swelling, and crosslinking the base mat in a polyalkyleneamine solution.

In addition, the method may further include, after step (a), (a") treating the base mat with a silane compound including an amine group.

In addition, the method may further include, after step (b), (b') forming an adhesive portion on a surface of the sensor for simultaneously measuring electrocardiogram and mechanocardiogram.

Example Embodiments

Hereinafter, preferred example embodiments will be described. However, this is for illustrative purposes, and the scope of the present disclosure is not limited thereby.

Preparation of Imidized Base Mat

Preparation Example 1: Base Mat (SEBS-g-MA)

Polystyrene-block-poly(ethylene butylene)-block-polystyrene grafted with maleic anhydride (SEBS-g-MA) (weight fraction of MA=2 wt %), cyclohexane, tetrahydrofuran (THF), and dimethylformamide (DMF) were mixed in a weight ratio of 10:63:9:18 to prepare a polymer solution.

The polymer solution was electrospun onto an aluminum foil at a fixed feed rate (1 mL/h), voltage (18.0 kV), and relative humidity (40%) using an electrospinning setup (Nano NC, South Korea). Here, the distance between a nozzle and a collector was 15 cm, and a 22 G nozzle was used. A base mat was prepared by peeling off the electrospun nanofiber coating (~100 μm in thickness) from the foil.

Preparation Example 2: Imidized Base Mat (SEBS-g-MA+b-PEI)

The base mat prepared according to Preparation Example 1 was immersed in a branched polyethyleneimine (b-PEI) solution (10 wt % in ethanol) for 10 hours at 70° C. Thereafter, the base mat was taken out of the solution and washed with distilled water under ultrasonication for 30 minutes to remove residual b-PEI, and then dried at room temperature to prepare an imidized base mat.

Manufacturing of Sensor for Simultaneously Measuring Electrocardiogram and Mechanocardiogram Example Embodiment 1

The imidized base mat prepared according to Preparation Example 2 was treated by oxygen plasma (O₂ plasma, 22 sccm, 200 W, 5 minutes) and immersed in a (3-aminopropyl) triethoxysilane (APTES) solution (10 wt % in ethanol) for 2 hours at 70° C. Thereafter, the imidized base mat was washed with distilled water under ultrasonication for 30 minutes.

After drying, Au was sputtered on the imidized base mat treated with the APTES through a polyethylene terephthalate film mask to form a conductive pattern portion including a first pattern for measuring electrocardiogram and a second pattern for measuring mechanocardiogram. As a result, a sensor for simultaneously measuring electrocardiogram and mechanocardiogram was obtained.

Here, the first pattern was formed by sputtering Au into a 3 mm wide line shape at 20 mA for 500 seconds, and the second pattern was formed by sputtering Au into a 3 mm wide "□" shape at 20 mA for 50 seconds.

Thereafter, PDMS prepolymer and a curing agent were mixed at a weight ratio of 10:1 to prepare a first mixture. Polyethyleneimine 80% ethoxylated solution (40 μL) was added to 20 g of the first mixture to prepare a second mixture. Before curing, the second mixture was applied on a surface of the sensor. The sensor with the second mixture was cured at 80° C. for 4 hours to form an adhesive portion.

TEST EXAMPLES

Test Example 1: Tensile Strength Test of Base Mat

Figure 4:
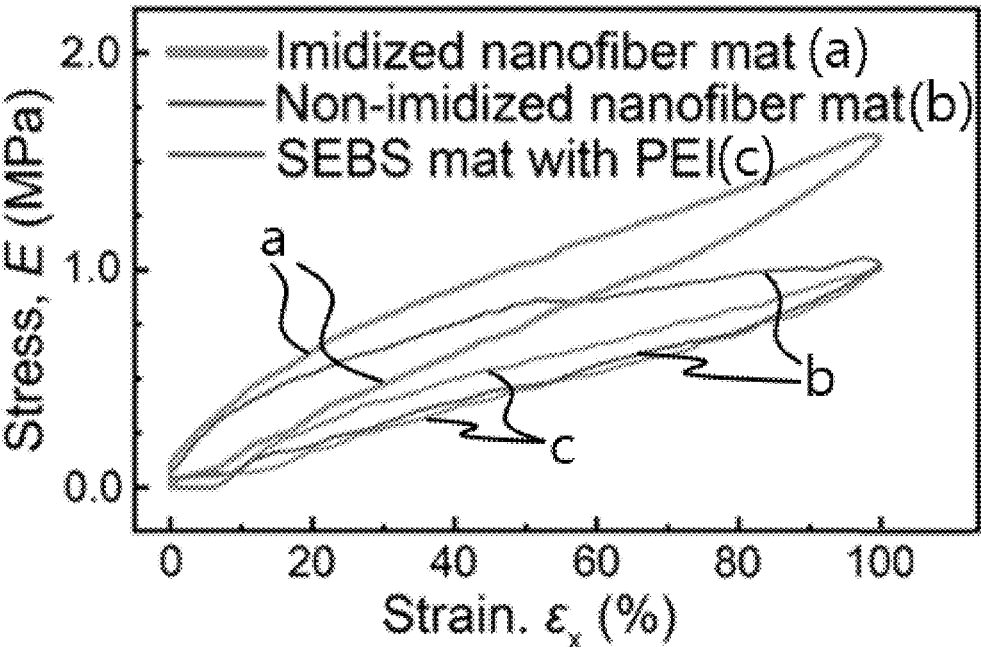
FIG. 4 is a view illustrating a stress-strain graph of an SEBS mat with PEI, a nanofiber mat of Preparation Example 1, and a nanofiber mat of Preparation Example 2 upon uniaxial stretching.

FIG. 4 is a view illustrating a stress-strain graph a polystyrene-block-poly(ethylene butylene)-block-polystyrene (SEBS) mat with polyethyleneimine (PEI), the nanofiber mat of Preparation Example 1, and the nanofiber mat of Preparation Example 2 upon uniaxial stretching; Referring to FIG. 4, it can be confirmed that Preparation Example 2 (imidized nanofiber mat), which is a base mat imidized by b-PEI, exhibits the best tensile strength.

In addition, through Preparation Example 2 (imidized nanofiber mat) and the SEBS mat with PEI, it can be confirmed that nanofibers included in the base mat were prepared using polystyrene-block-poly(ethylene butylene)-block-polystyrene grafted with maleic anhydride, so the maleic anhydride group and PEI were crosslinked.

Test Example 2: Confirmation of Pattern Thickness Difference Depending on Au Sputtering Time FIG. 5 is a view illustrating cross-sectional scanning electron microscope (SEM) and energy dispersive X-ray spectroscopy (EDS) elemental mapping images of the first pattern (top) and the second pattern (bottom) of Example Embodiment 1.

Figure 5:
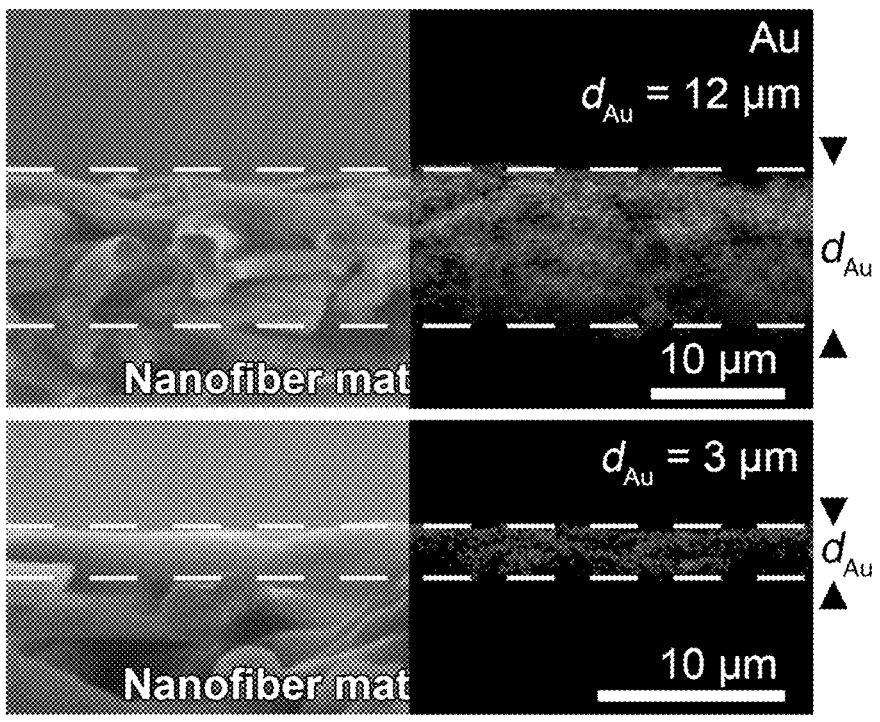
FIG. 5 is a view illustrating cross-sectional SEM and EDS elemental mapping images of a first pattern (top) and a second pattern (bottom) of Example Embodiment 1.

Referring to FIG. 5, it can be confirmed that the first pattern formed by sputtering Au for 500 seconds has a thickness of about 12 μm, and the second pattern formed by sputtering Au for 50 seconds has a thickness of about 3 μm.

In addition, it can be confirmed that each of the first pattern and the second pattern includes nanofibers and a conductor (Au) located between the nanofibers.

Figure 6A:
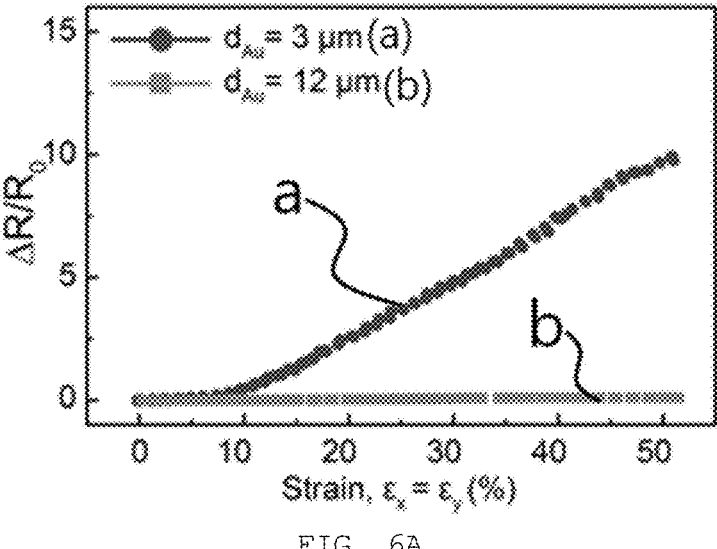
FIG. 6A is a view illustrating a graph of the relative resistance changes of Example Embodiment 1 during biaxial stretching at 50%.
Figure 6B:
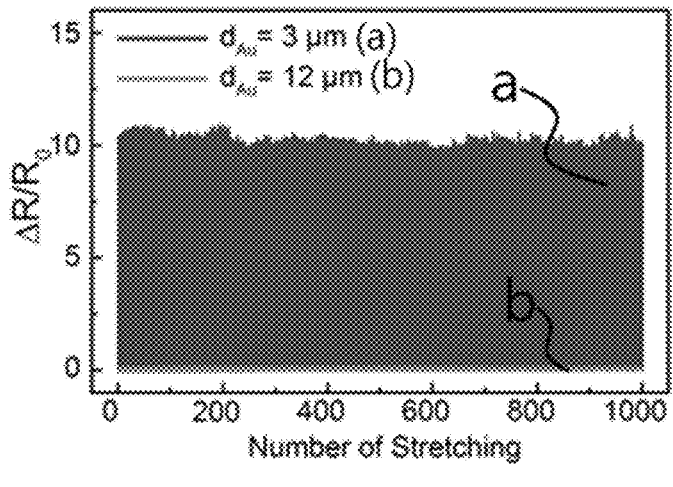
FIG. 6B is a view illustrating a graph of the relative resistance changes of Example Embodiment 1 during 1,000 cycles of biaxial stretching at 50%.
Figure 6B:
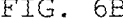

Test Example 3: Measurement of Relative Resistance Changes Upon Stretching of Sensor FIG. 6A is a view illustrating a graph of the relative resistance changes of Example Embodiment 1 during biaxial stretching at 50%. FIG. 6B is a view illustrating a graph of the relative resistance changes of Example Embodiment 1 during 1,000 cycles of biaxial stretching at 50%.

Referring to FIG. 6A, in Example Embodiment 1, it can be confirmed that the first pattern ($d_{Au}$=12 μm) showed negligible resistance change up to $\varepsilon_x=\varepsilon_y=50\%$, whereas the second pattern ($d_{Au}$=3 μm) was sensitive to the strain with a gauge factor of 19.2.

In addition, it can be confirmed that the two patterns both showed no electrical hysteresis, indicating that the nanofiber mat was elastic without remnant strain after the stress was released.

Referring to FIG. 6B, it can be confirmed that the resistance changes of the first pattern and the second pattern were highly reliable during 1,000 cycles of biaxial stretching at $\varepsilon_x=\varepsilon_y=50\%$.

This result indicates that it is possible to manufacture strain-independent stretchable electrodes used for electrocardiogram (ECG) sensing and a strain-sensitive conductor used for mechanocardiogram (MCG) sensing by simply adjusting the Au sputtering time.

Test Example 4: Confirmation of Formation of Adhesive Portion

Figure 7:
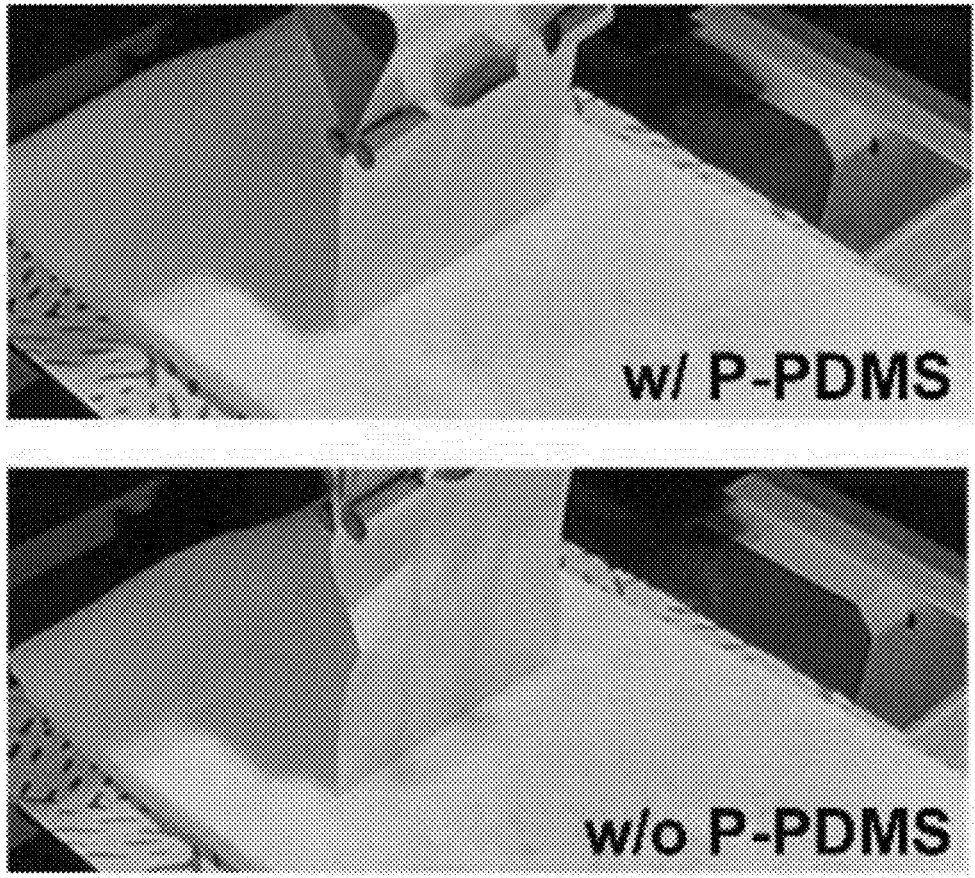
FIG. 7 is a view illustrating images of a 90 peel-off test for Example Embodiment 1 with and without an adhesive portion (w/(P-PDMS), w/o P-PDMS)

FIG. 7 is a view illustrating images of a 90 peel-off test for Example Embodiment 1 with and without an adhesive portion (w/ethoxylated polyethylenimine with polydimethylsiloxane (P-PDMS), w/o P-PDMS). In detail, FIG. 7 illustrates the comparison results of the 90° peel-off test of the sensors according to Example Embodiment 1 with and without the adhesive portion (P-PDMS) when they were placed on a subcutaneous porcine skin.

Figure 8:
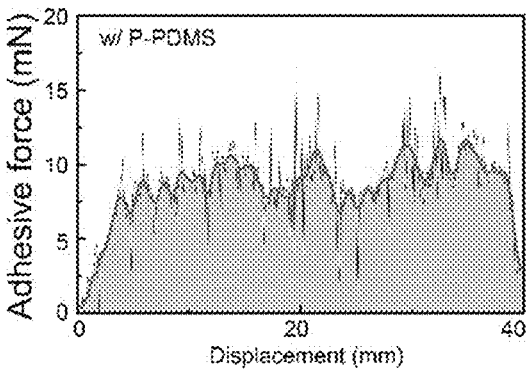
FIG. 8 is a view illustrating graphs of the adhesive force obtained by the 90 peel-off test for Example Embodiment 1 with and without the adhesive portion (w/P-PDMS, w/o P-PDMS)
Figure 8:
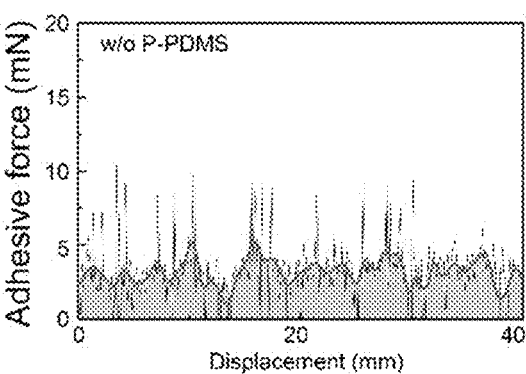

FIG. 8 is a view illustrating graphs of the adhesive force obtained by the 90 peel-off test for Example Embodiment 1 with and without the adhesive portion (w/P-PDMS, w/o P-PDMS).

Referring to FIG. 8, it can be confirmed that the adhesive portion (P-PDMS) provides sufficient adhesion to the tissue so that it can effectively prevent the movement of the sensor on the tissue.

Test Example 5: Confirmation of Whether Sensor is Subcutaneously Implantable FIG. 9B is a view illustrating images of Example Embodiment 1 attached onto the subcutaneous muscle (left: before covering the skin layer, right: 1 hour after covering the skin layer).

Figure 9A:
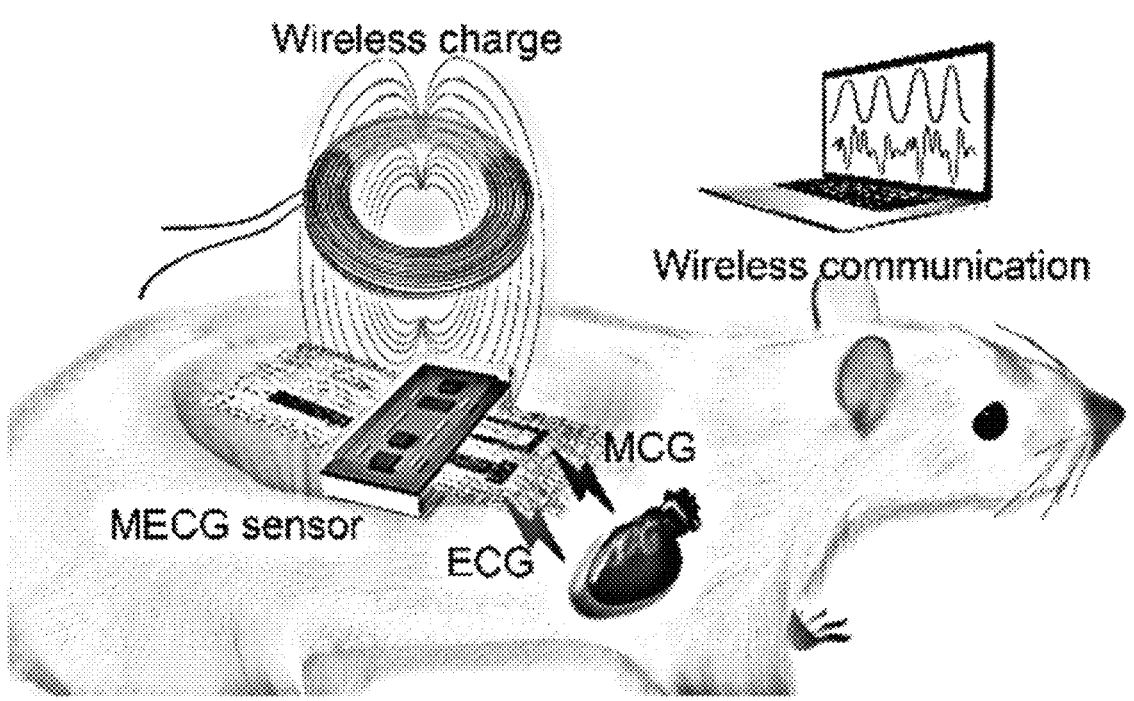
FIG. 9A is a schematic view illustrating a subcutaneously implantable MECG sensor with wireless communication and a charging system.
Figure 9B:
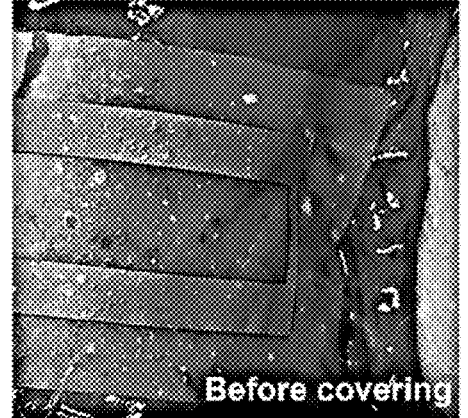
FIG. 9B is a view illustrating images of Example Embodiment 1 attached onto the subcutaneous muscle (left: before covering the skin layer, right: 1 hour after covering the skin layer)
Figure 9B:
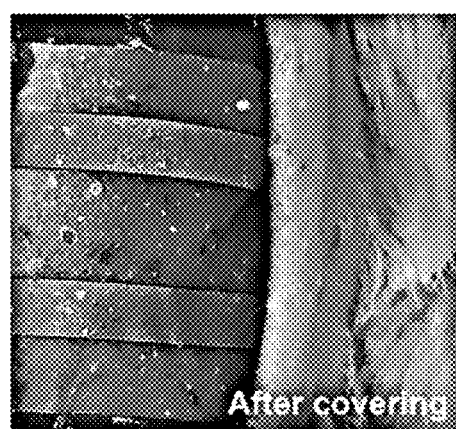

Referring to FIG. 9B, the sensor according to Example Embodiment 1 was conformally contacted to the muscle tissue immediately upon contact due to deformability and water permeability thereof, and maintained the contact after being covered with the skin tissue.

Figure 9C:
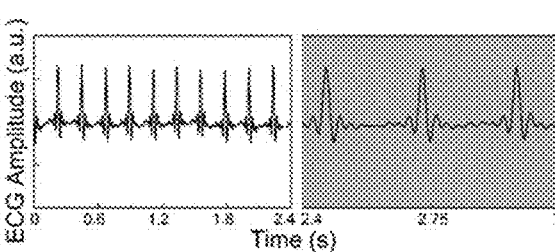
FIGS. 9C to 9E are views illustrating graphs of filtered ECG (left) and MCG (right) signals from the MECG sensor, in which the profiles were obtained before phenylephrine injection (FIG. 9C), after phenylephrine injection (FIG. 9D), and after recovery (FIG. 9E), the grey boxes indicate enlarged images of each waveform, the red circles indicate the signals used as the MECG profiles, and the red box in FIG. 9C indicates the signals from respiration.
Figure 9C:
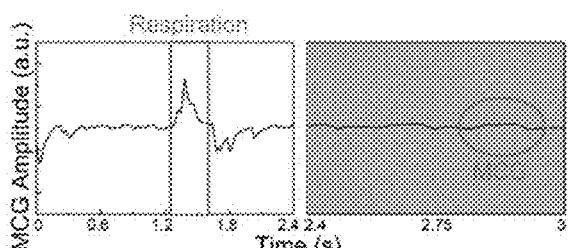
Figure 9D:
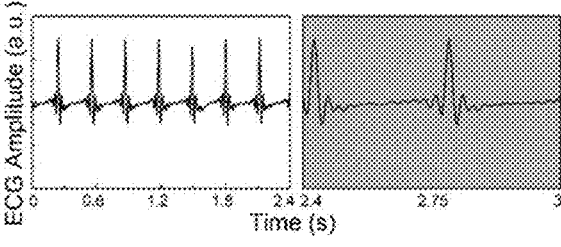
Figure 9D:
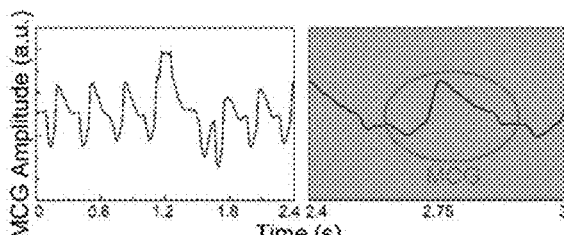
Figure 9E:
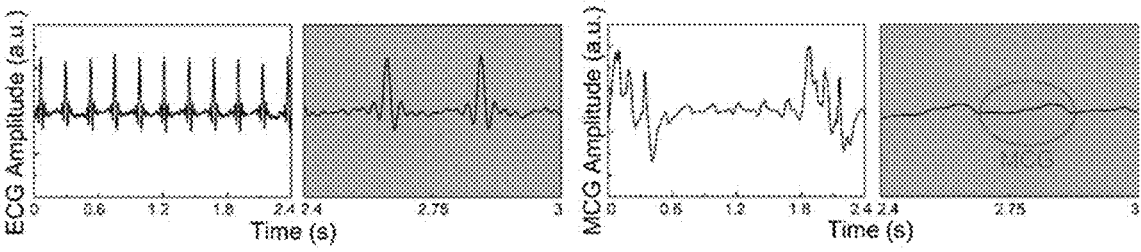

Test Example 6: Confirmation of Simultaneous Measurement of Electrocardiogram and Mechanocardiogram FIGS. 9C to 9E are views illustrating graphs of filtered electrocardiogram (ECG) (left) and mechanocardiogram (MCG) (right) signals from a sensor for simultaneously measuring electrocardiogram (ECG) and mechanocardiogram (MCG) (hereinafter, referred to as "mechano-electrocardiogram (MECG) sensor"), in which the profiles were obtained before phenylephrine injection (FIG. 9C), after phenylephrine injection (FIG. 9D), and after recovery (FIG. 9E), the grey boxes indicate enlarged images of each waveform, the red circles indicate the signals used as the MECG profiles, and the red box in FIG. 9C indicates the signals from respiration.

Figure 10A:
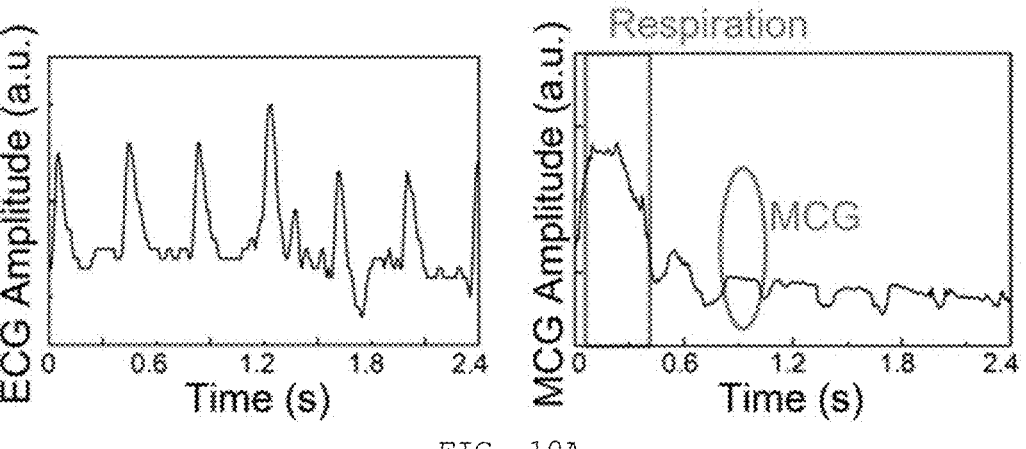
FIG. 10A is a view illustrating graphs of the ECG and MCG signals measured immediately after implanting the MECG sensor, in which in MCG data, the large waveform in the red box is induced by respiration and the small waveform in the red circle is induced by cardiac movement.
Figure 10B:
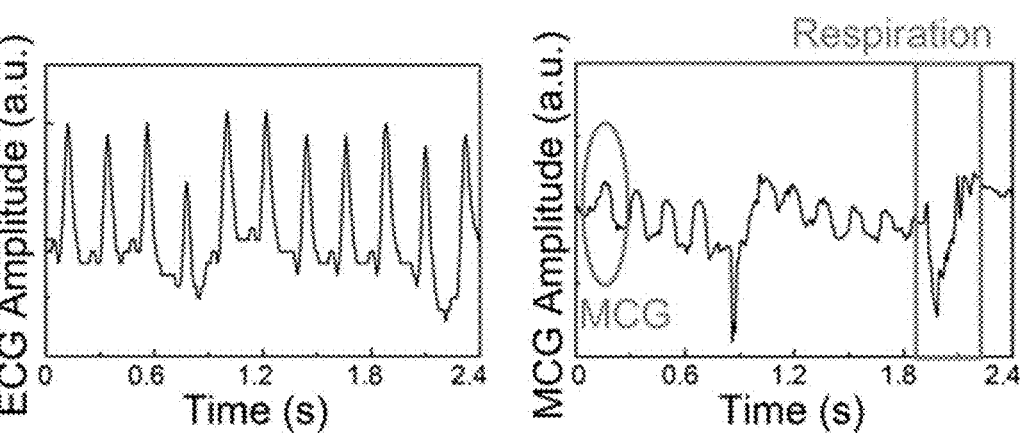
FIG. 10B is a view illustrating graphs of the ECG and MCG signals measured after 1 day of implantation.

FIG. 10A is a view illustrating graphs of the ECG and MCG signals measured immediately after implanting the MECG sensor, in which in MCG data, the large waveform in the red box is induced by respiration and the small waveform in the red circle is induced by cardiac movement. FIG. 10B is a view illustrating graphs of the ECG and MCG signals measured after 1 day of implantation.

Figure 11A:
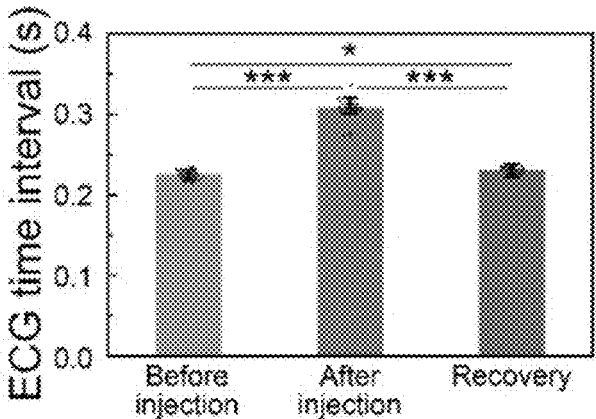
FIG. 11A is a view illustrating a graph of the ECG time interval for the three states of before phenylephrine injection, after phenylephrine injection, and after recovery for Example Embodiment 1 attached on the muscle tissue.
Figure 11B:
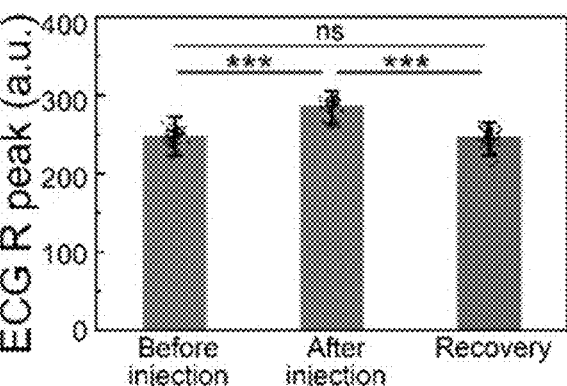
FIG. 11B is a view illustrating a graph of the ECG R peak intensity for the three states of before phenylephrine injection, after phenylephrine injection, and after recovery for Example Embodiment 1 attached on the muscle tissue.
Figure 11C:
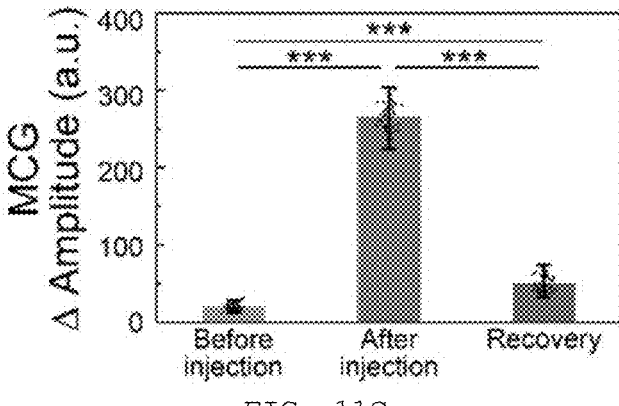
FIG. 11C is a view illustrating a graph of the MCG waveform amplitude for the three states of before phenylephrine injection, after phenylephrine injection, and after recovery for Example Embodiment 1 attached on the muscle tissue.
Figures 11D, 11E, 11F:
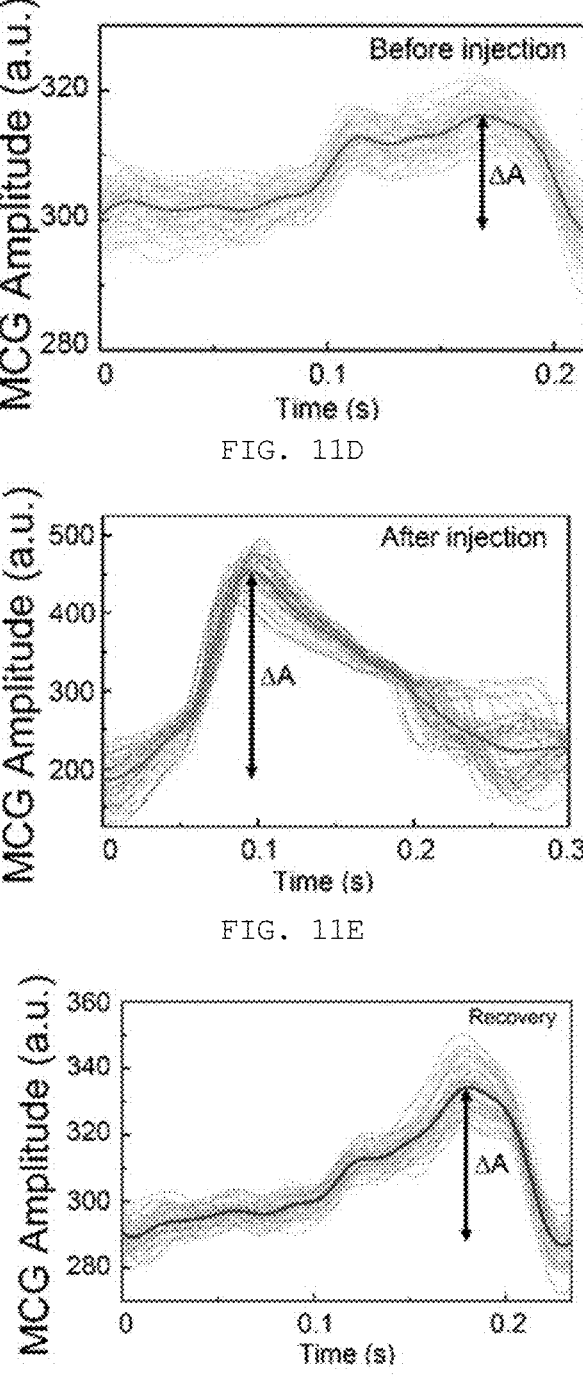
FIGS. 11D to 11F are views illustrating graphs of the mean waveform ensembles (bold) from a large number of MCG waveforms according to the heart beat cycle for the three states: before phenylephrine injection, after phenylephrine injection, and after recovery, in which the black arrows indicate the relative MCG waveform amplitude difference.

FIG. 11A is a view illustrating a graph of the ECG time interval for the three states of before phenylephrine injection, after phenylephrine injection, and after recovery for Example Embodiment 1 attached on the muscle tissue. FIG. 11B is a view illustrating a graph of the ECG R peak intensity for the three states of before phenylephrine injection, after phenylephrine injection, and after recovery for Example Embodiment 1 attached on the muscle tissue. FIG. 11C is a view illustrating a graph of the MCG waveform amplitude for the three states of before phenylephrine injection, after phenylephrine injection, and after recovery for Example Embodiment 1 attached on the muscle tissue. FIGS. 11D to 11F are views illustrating graphs of the mean waveform ensembles (bold) from a large number of MCG waveforms according to the heart beat cycle for the three states: before phenylephrine injection, after phenylephrine injection, and after recovery, in which the black arrows indicate the relative MCG waveform amplitude difference.

Figure 10C:
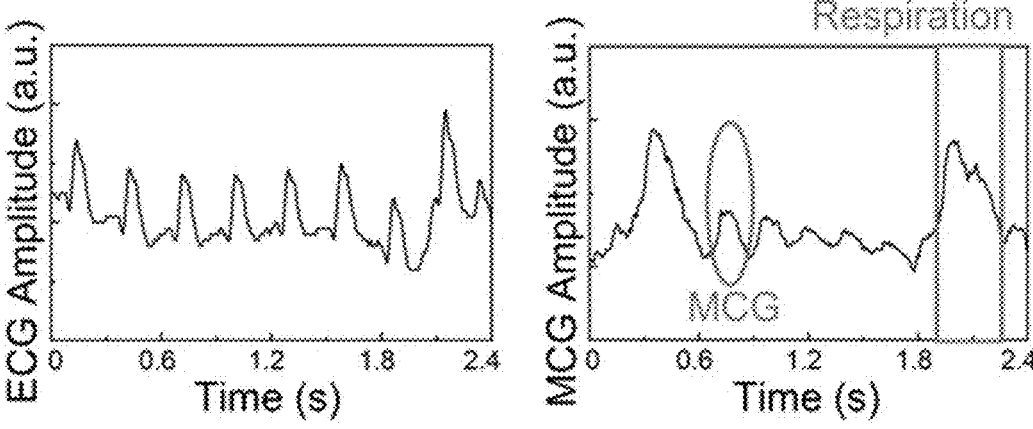
FIG. 10C is a view illustrating graphs of the ECG and MCG signals measured after 2 days of implantation.

Referring to FIGS. 10A to 10C, as a result of measuring the ECG and MCG signals for 3 days, it was confirmed that they were produced normally from the MECG sensor even when a rat moved freely after implantation.

Referring to FIGS. 9C to 9E and 11A to 11F, multiple waveforms were obtained for 20 seconds according to the heart beat period measured from the ECG R peak period (0.225 seconds before injection, 0.308 seconds after injection, 0.230 seconds after recovery). Although the heart rate and R peak slightly increased immediately after phenylephrine injection, the difference was not significant. In addition, for the MCG changes and the MCG waveforms, the waveforms were in good coincidence before injection and after recovery. The ensemble profiles (bold) well represented the MCG waveforms obtained in each state. The average value of the MCG waveform amplitude before phenylephrine injection was 19.8, but it increased to 266.3 immediately after phenylephrine injection and then slowly approached to the normal (e.g., 49.4 in 4 minutes after injection).

This result indicates that the sensor manufactured according to the present disclosure can simultaneously and independently measure the ECG and the MCG.

Figure 12A:
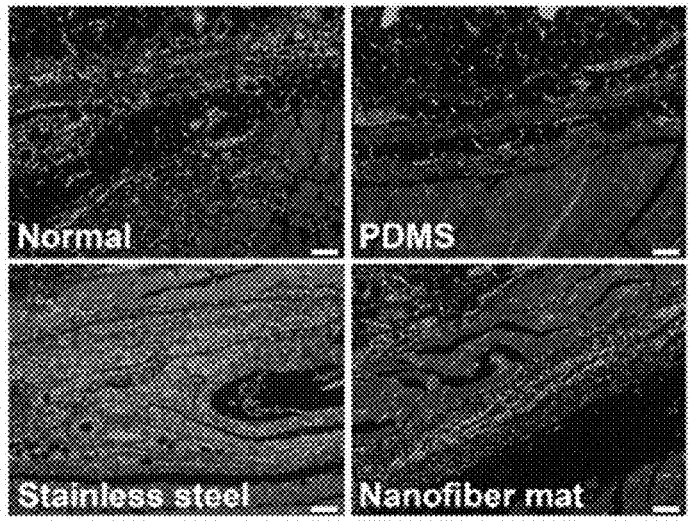
FIG. 12A is a view illustrating CTGF immunofluorescence images of the rat muscle tissue obtained after an Au-patterned nanofiber mat was implanted for 2 weeks, in which polydimethylsiloxane (PDMS) and stainless steel were implanted for comparison, CTGF was represented by red, DAPI was represented by blue, and normal control samples were compared (scale bar=100 μm)
Figure 12B:
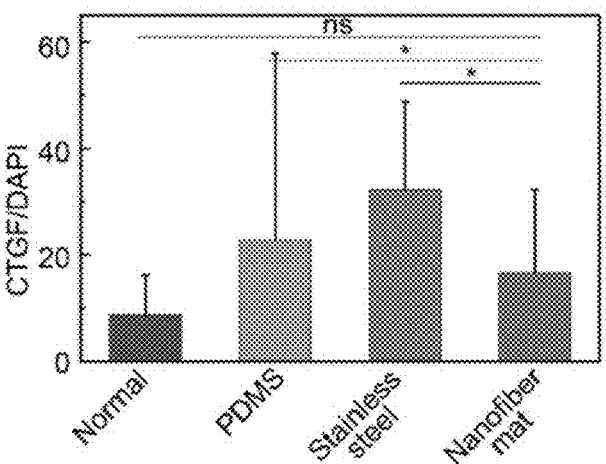
FIG. 12B is a view illustrating a graph of quantification of the relative CTGF fluorescence intensity.
Figure 12C:
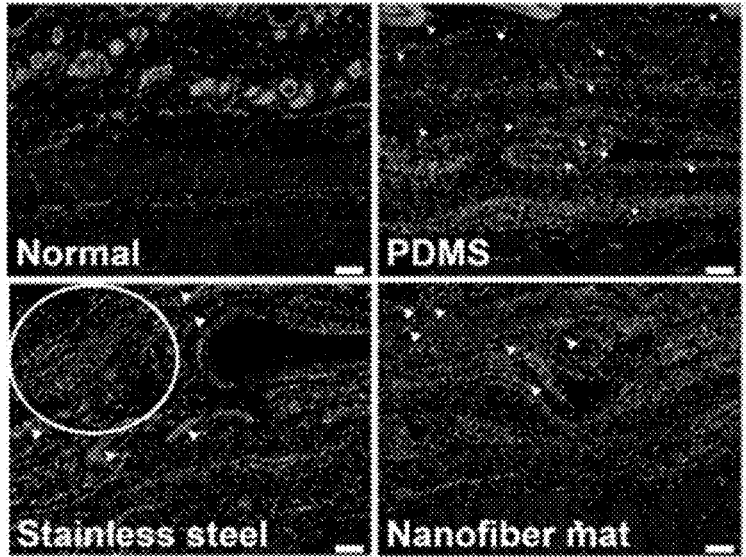
FIG. 12C is a view illustrating CD68 immunofluorescence images of the rat muscle tissue after 2 weeks of implantation, in which the white circle and arrows indicate inflammation responses (scale bar=100 μm), CD68 was represented by red, and DAPI was represented by blue.
Figure 12D:
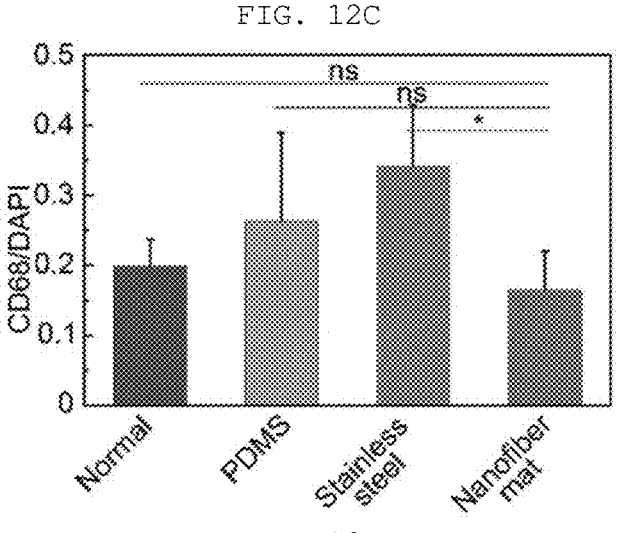
FIG. 12D is a view illustrating a graph of quantification of the relative CD68 fluorescence intensity.

Test Example 7: Confirmation of Biocompatibility of Au-Patterned Nanofiber Mat FIG. 12A is a view illustrating connective tissue growth factor (CTGF) immunofluorescence images of the rat muscle tissue obtained after an Au-patterned nanofiber mat was implanted for 2 weeks. FIG. 12B is a view illustrating a graph of quantification of the relative CTGF fluorescence intensity. FIG. 12C is a view illustrating cluster of differentiation 68 (CD68) immunofluorescence images of the rat muscle tissue after 2 weeks of implantation. FIG. 12D is a view illustrating a graph of quantification of the relative CD68 fluorescence intensity.

Referring to FIGS. 12A to 12D, the Au-patterned nanofiber mat was implanted in the subcutaneous muscle tissue of a rat for 2 weeks. Conventional stainless steel electrodes and PDMS were also implanted for comparison. In the case of the Au-patterned nanofiber mat, the expression level of CTGF was not significantly different from the normal control, but showed a significant difference when compared to stainless steel and PDMS. CD68 is a protein expressed in the cells that experience inflammatory responses and phagocytosis, such as monocytes and macrophages. When comparing and analyzing the expression level of CD68, the nanofiber mat showed no significant difference from normal tissue and PDMS, but showed a significant difference from stainless steel. It is noteworthy that the high CD68/DAPI intensity of the normal sample was caused by nonspecific staining of the red blood cells or autofluorescence in the hair follicle and blood vessel. Such regions could not be completely excluded for the expression level measurement, so the CD68/DAPI intensity of the normal sample appeared to be higher than the nanofiber mat sample.

This result indicates that the Au-patterned SEBS-g-MA nanofiber mat is a good substrate material for implantable electrodes because it has a lower modulus and lower friction than conventional electrodes. The moduli of the nanofiber mat (100 μm in thickness) were 22.7 kPa and 1.74 MPa, respectively. The static friction coefficients were similar: 1.01 for the nanofiber mat and 1.09 for the PDMS layer. Since no inflammatory reaction was observed, it was confirmed that the sensor according to the present disclosure is biocompatible in subcutaneous use.

Figure 13A:
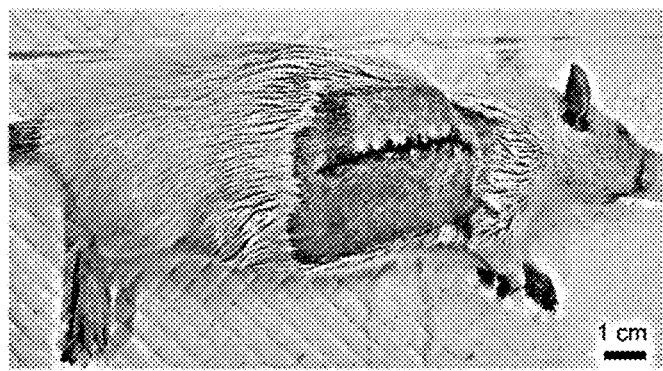
FIG. 13A is a view illustrating an image of a rat implanted with a fully implanted MECG sensor with a microcontroller unit board and MECG signals.
Figure 13B:
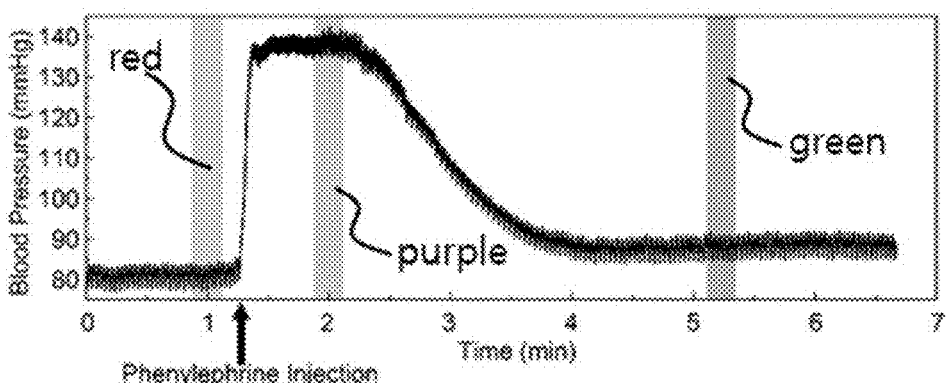
FIG. 13B is a view illustrating a graph of the blood pressure change from the femoral artery of the rat, in which the colored boxes indicate the region where which the MECG data was extracted (red: before phenylephrine injection, purple: after phenylephrine injection, green: after recovery)
Figure 13C:
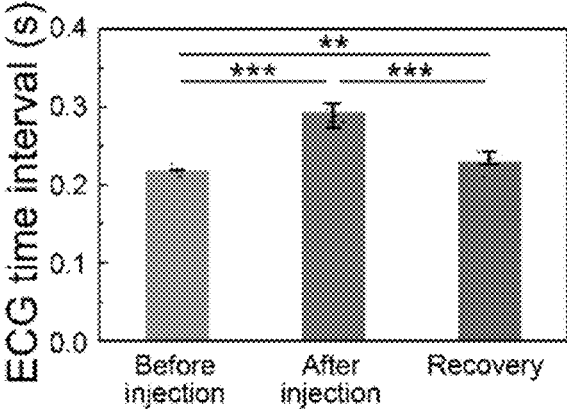
FIG. 13C is a view illustrating a graph of the ECG time interval for the three states of before phenylephrine injection, after phenylephrine injection, and after recovery.
Figure 13D:
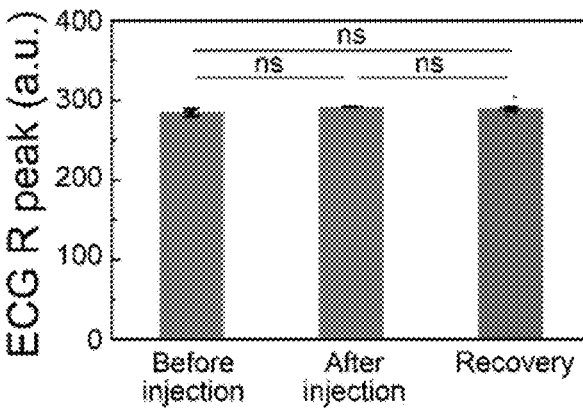
FIG. 13D is a view illustrating a graph of the relative ECG R peak intensity.
Figure 13E:
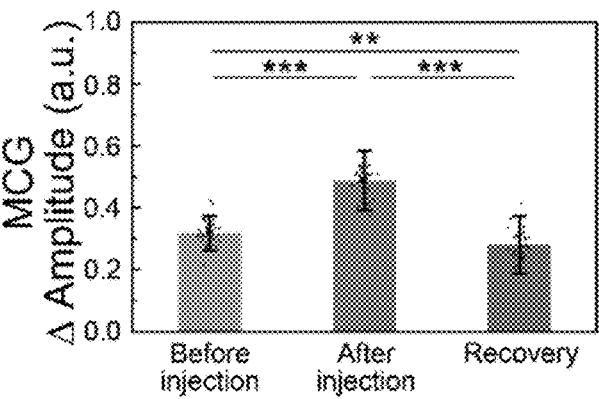
FIG. 13E is a view illustrating a graph of the relative MCG waveform amplitude difference.
Figure 13F:
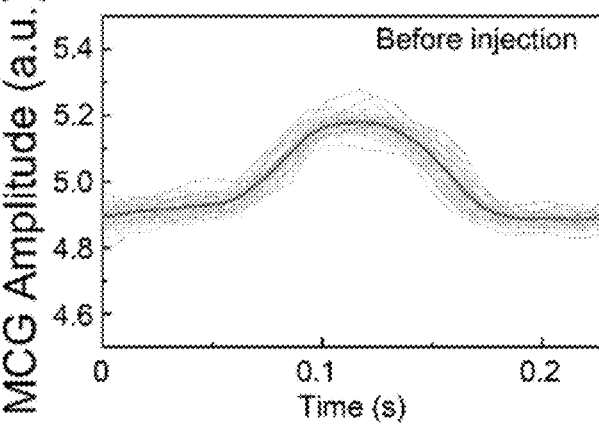
FIGS. 13F to 13H are views illustrating graphs of the mean waveform ensembles (bold) from a large number of MCG waveforms according to the heart beat cycle for the three states: before phenylephrine injection, after phenylephrine injection, and after recovery.
Figures 13G, 13H:
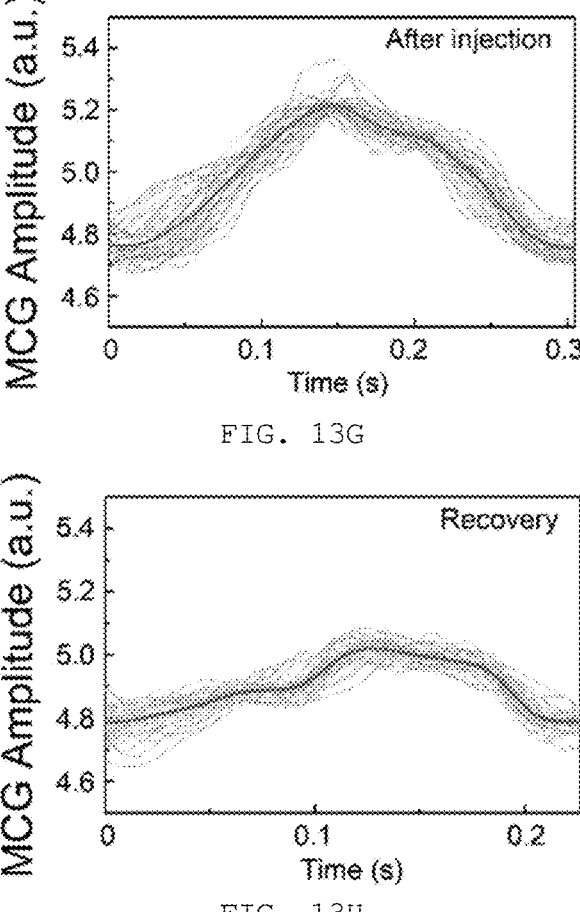

Test Example 8: Confirmation of MECG Signal Acquisition from Implantable MECG Sensor FIG. 13A is a view illustrating an image of a rat implanted with a fully implanted MECG sensor with a microcontroller unit (MCU) board and MECG signals. FIG. 13B is a view illustrating a graph of the blood pressure change from the femoral artery of the rat, in which the colored boxes indicate the region where which the MECG data was extracted (red: before phenylephrine injection, purple: after phenylephrine injection, green: after recovery). FIG. 13C is a view illustrating a graph of the ECG time interval for the three states of before phenylephrine injection, after phenylephrine injection, and after recovery. FIG. 13D is a view illustrating a graph of the relative ECG R peak intensity. FIG. 13E is a view illustrating a graph of the relative MCG waveform amplitude difference. FIGS. 13F to 13H are views illustrating graphs of the mean waveform ensembles (bold) from a large number of MCG waveforms according to the heart beat cycle for the three states: before phenylephrine injection, after phenylephrine injection, and after recovery.

Referring to FIGS. 13A to 13H, the MECG sensor and MCU for wireless communication and power transmission were implanted subcutaneously and the skin was sutured. Because of the significant space between the rat's skin and muscle tissue, the entire device could be implanted and secured. A separate wireless data acquisition system was developed, and the same MCU development board used in the implantable device was used as a receiver. The receiver receives data from the implantable device via BLE communication and is connected to a PC for real-time data processing. Data is stored in the PC and processed using LabVIEW. Due to a small-sized antenna of the implantable device and signal attenuation in the tissue, the communication range has been shortened compared to in the air. However, by placing the receiver near a cage, data could be successfully acquired from the rat moving freely inside the cage. Depending on the application, using a lower frequency band or optimizing the antenna part can increase the communication range. The MECG signals were acquired through blood pressure measurement. The blood pressure increased momentarily after injection of phenylephrine, and then gradually decreased over time and reached the normal state within 4 minutes after injection. The MECG signals were acquired for the three states: before injection, after injection, and after recovery. Referring to FIGS. 13C and 13D, as observed when the sensor was attached to the tissue without suturing, the heart rate decreased due to phenylephrine injection and the R peak value in the ECG waveforms was almost unchanged. Referring to FIG. 13E, the amplitude of the MCG waveform increased from 0.38 to 0.53 as blood pressure increased after phenylephrine injection and then it decreased to 0.35 after the normal blood pressure was recovered. This results indicates that the MCG signal is closely related to the blood pressure. Referring to FIGS. 13F to 13H, the MCG profiles showed reliable sensing profiles for the three states: before injection, after injection, and after recovery. The reduced magnitude difference in the MCG profiles is due to the large respiration signals as a background profile.

The present disclosure proposes a subcutaneous mechanocardiogram (MECG) sensor that simultaneously obtains electrocardiogram (ECG) and mechanocardiogram (MCG). The sensor uses two Au patterns on a stretchable nanofiber mat. The one for an ECG electrode is not sensitive to strain, and the one for an MCG electrode is sensitive to strain. The sensor was connected to a microcontroller for wireless communication and charging. The porous biocompatible sensor was adhered immediately to the subcutaneous tissue with minimal immune response. By monitoring ECG and MCG signals before and after drug injection, it was confirmed that the MECG sensor can provide complementary diagnosis of cardiovascular disease in a more comprehensive manner than the ECG use only.

The scope of the present disclosure is defined by the appended claims rather than the description which is presented above. Moreover, the present disclosure is intended to cover not only the exemplary embodiments, but also various alternatives, modifications, equivalents and other embodiments that may be included within the spirit and scope of the present disclosure as defined by the appended claims.

What is claimed is:

1. A sensor for simultaneously measuring electrocardiogram and mechanocardiogram, the sensor comprising:
   a base mat including nanofibers including a polymer, and having a porous structure; and
   a conductive pattern portion impregnated into the base mat to a predetermined depth and including a first pattern for measuring the electrocardiogram and a second pattern for measuring the mechanocardiogram,
   wherein each of the first pattern and the second pattern includes: nanofibers including the polymer; and a conductor located between the nanofibers,
   wherein the nanofibers of the base mat, the nanofibers of the first pattern, and the nanofibers of the second pattern are the same,
   wherein the first pattern has a thickness in a range of 10 to 20 μm, and
   the second pattern has a thickness in a range of 1 to 8 μm.

2. The sensor of claim 1, wherein the polymer of the base mat is bound to the polymer of the conductive pattern portion by chain entanglement or covalent bonding.

3. The sensor of claim 1, wherein the first pattern has a width larger than that of the second pattern.

4. The sensor of claim 1, wherein the first pattern has a width in a range of 500 μm to 5 mm, and the second pattern has a width in a range of 500 μm to 5 mm.

5. The sensor of claim 1, wherein the nanofibers of the base mat, the nanofibers of the first pattern, and the nanofibers of the second pattern each independently further includes a polyalkyleneamine obtained by crosslinking the polymer.

6. The sensor of claim 5, wherein the crosslinking each independently includes at least one selected from the group consisting of inter-crosslinking which crosslinks surfaces of the nanofibers with each other and intra-crosslinking which crosslinks the polymer within a single nanofiber.

7. The sensor of claim 1, wherein surfaces of the nanofibers are treated with a silane compound including an amine group.

8. The sensor of claim 1, wherein the polymer is an elastic body.

9. The sensor of claim 8, wherein the polymer further includes an organic acid anhydride grafted to a main chain.

10. The sensor of claim 1, wherein the conductor includes at least one selected from the group consisting of gold (Au), silver (Ag), copper (Cu), platinum (Pt), palladium (Pd), nickel (Ni), indium (In), aluminum (Al), iron (Fe), rhodium (Rh), ruthenium (Ru), osmium (Os), cobalt (Co), molybdenum (Mo), zinc (Zn), vanadium (V), tungsten (W), titanium (Ti), manganese (Mn), chromium (Cr), graphene, and carbon nanotubes (CNT).

11. The sensor of claim 1, further comprising:

an adhesive portion located on a surface of the sensor.

12. The sensor of claim 1, wherein the sensor is a subcutaneously implantable sensor.

\* \* \* \* \*